United States Patent [19]

Chou et al.

[11] Patent Number: 4,865,047

[45] Date of Patent: Sep. 12, 1989

[54] HYPERTHERMIA APPLICATOR

[75] Inventors: Chung-Kwang Chou, Arcadia, Calif.; Qiang-Rong Zhong, Guang-Zhou, China

[73] Assignee: City of Hope, Duarte, Calif.

[21] Appl. No.: 213,921

[22] Filed: Jun. 30, 1988

[51] Int. Cl.$^4$ .............................................. A61N 5/02
[52] U.S. Cl. ................................... 128/784; 128/401; 128/788; 128/804
[58] Field of Search ................ 128/784, 788, 804, 401

[56] References Cited

U.S. PATENT DOCUMENTS 4,612,940 9/1986 Kasevich et al. ..................... 128/804
4,658,836 4/1987 Turner ................................. 128/804

FOREIGN PATENT DOCUMENTS 0105677 4/1984 European Pat. Off. ............ 128/804

*Primary Examiner*—Lee S. Cohen
*Attorney, Agent, or Firm*—Edward S. Irons

[57] ABSTRACT

An intracavitary hyperthermic applicator comprising outer and inner coaxial conductors, electrical insulation between the conductors, the outer conductor terminating in a distal end spaced proximally from the distal end of the inner conductor, the outer conductor being slotted at a location spaced from the distal end of the outer conductor, defining a junction, outer and inner tubular sleeves of conductive material disposed coaxially over a length of the outer conductor, electrical insulation between the sleeves and between the inner sleeve and the outer conductor, conductive attachments securing the proximal ends of the sleeves to the outer conductor, and the outer sleeve terminating in a distal end spaced proximally from the distal end of the inner sleeve.

11 Claims, 4 Drawing Sheets

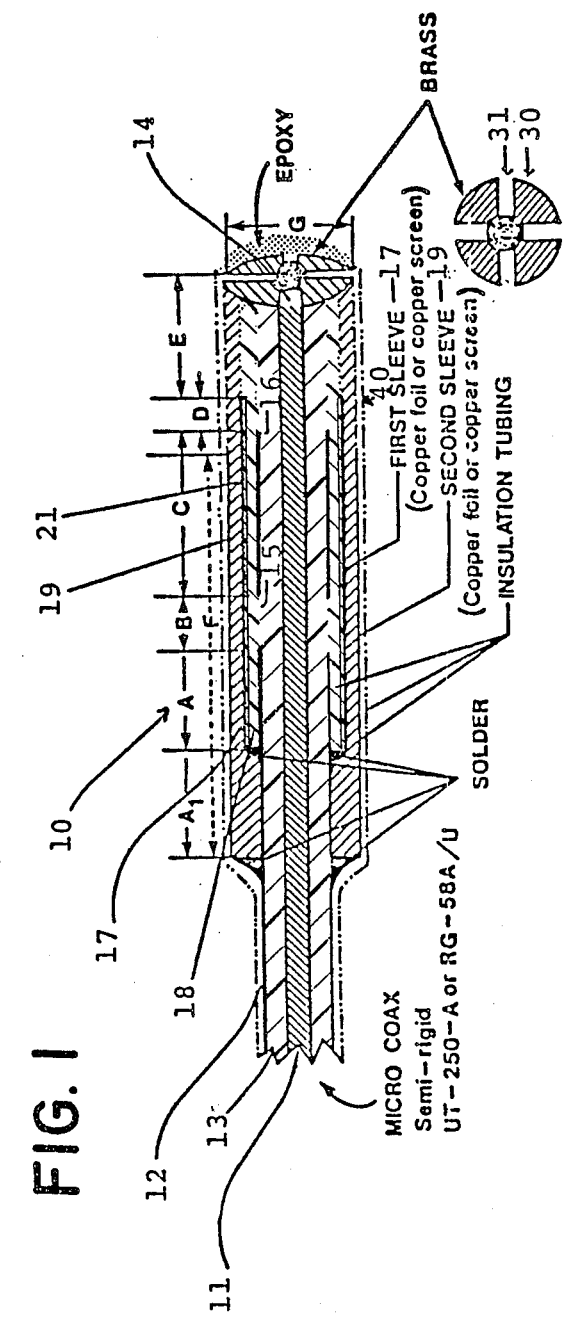

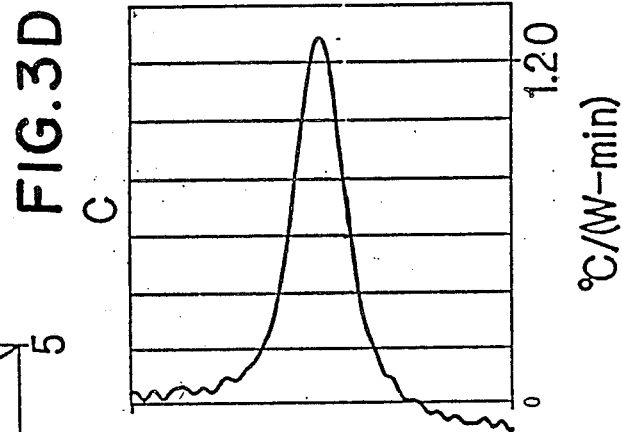
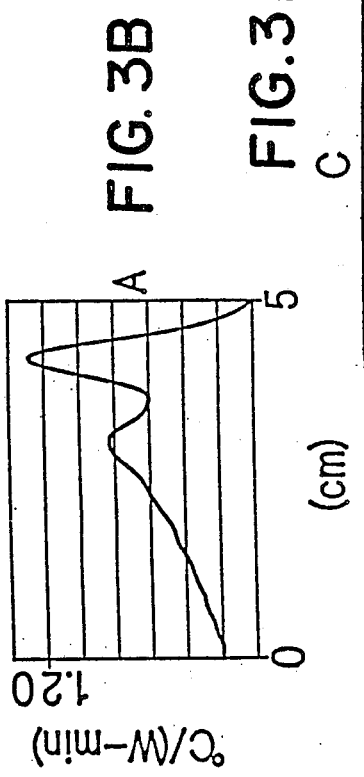
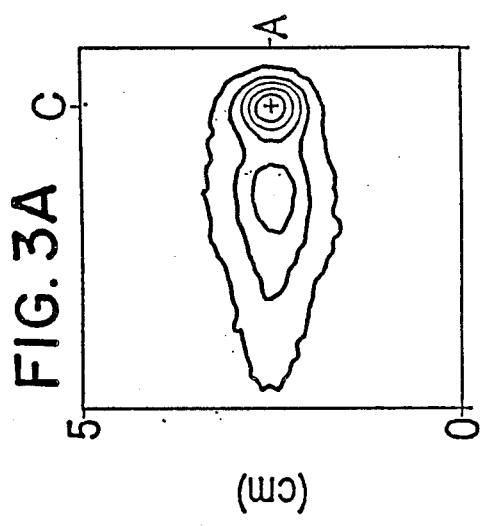
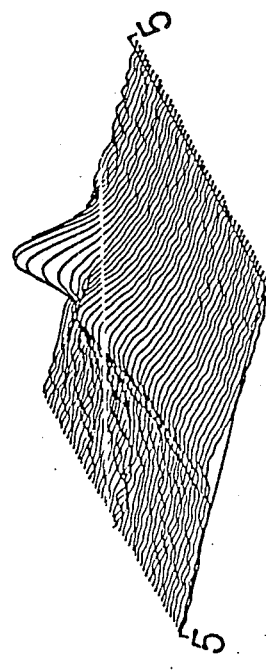
Intracavitary Applicator for Nasopharyngeal Cancer 915 MHz.
FIG. 3A
FIG. 3B
FIG. 3C
FIG. 3D
FIG. 3E

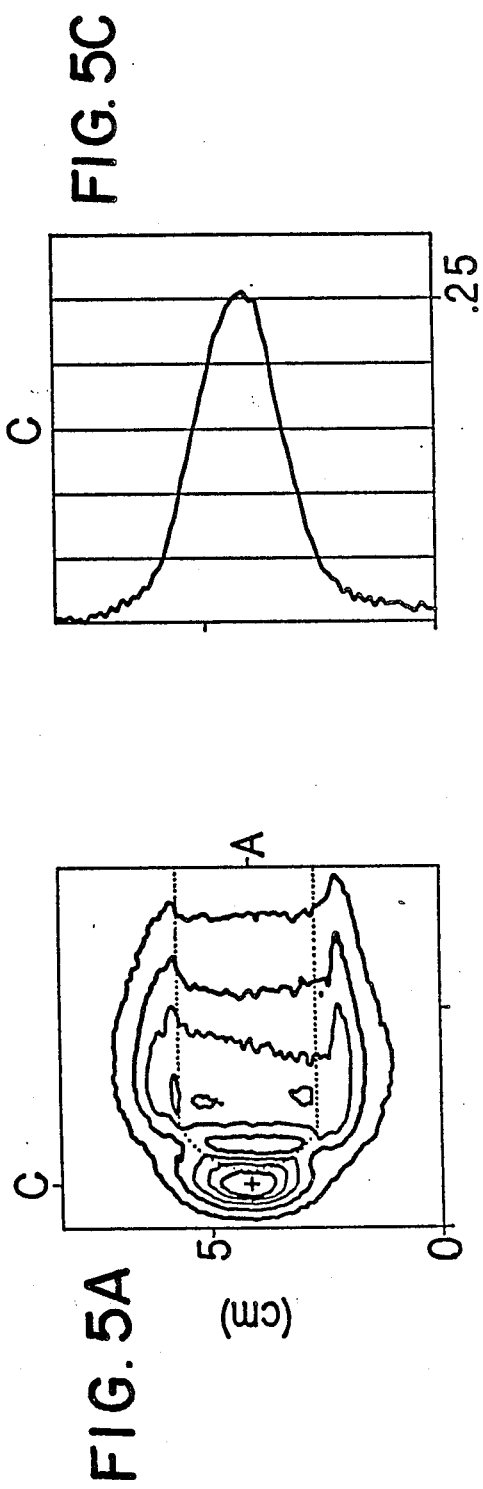
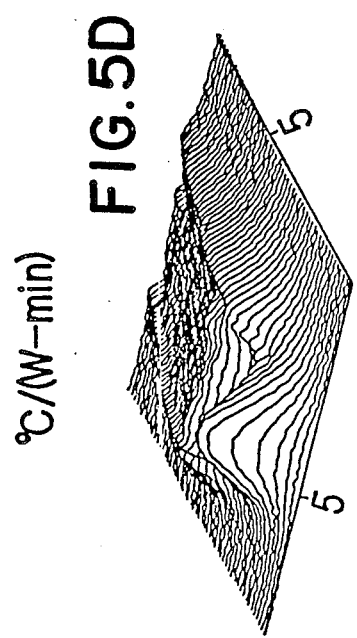
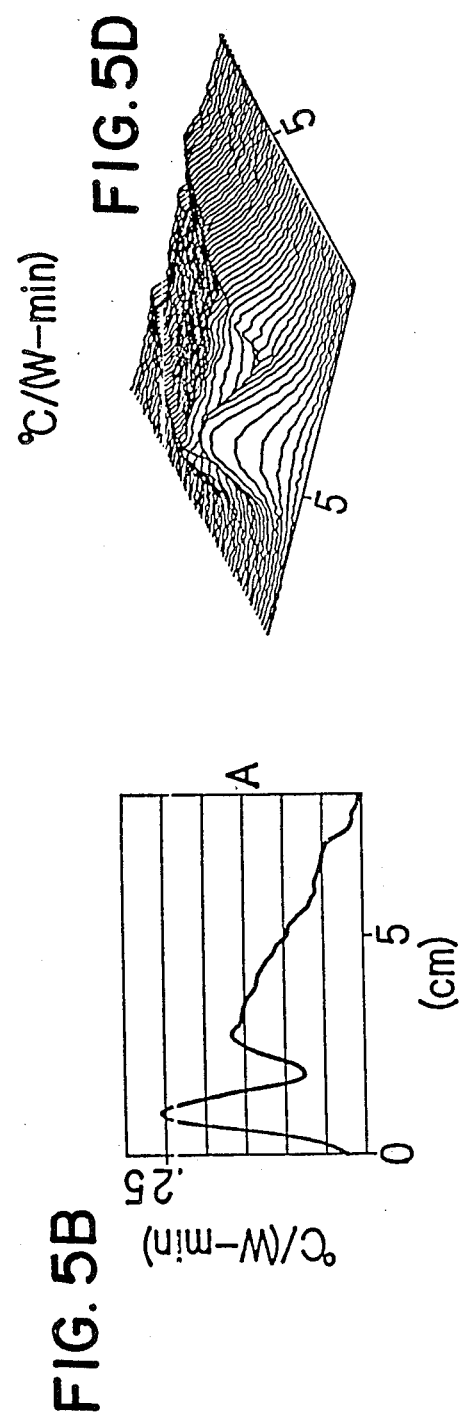
FIG. 5A  FIG. 5C  FIG. 5B  FIG. 5D
Intracavitary Cervical Cancer Applicator 915 MHz.

HYPERTHERMIA APPLICATOR

FIELD OF THE INVENTION

This invention relates to intracavitary hyperthermia applicators for use in nearly closed-end cavities such as the nasopharynx and the cervix.

BACKGROUND OF THE INVENTION

Interstitial insertion of catheters to apply therapeutic radiation and hyperthermia is commonplace. Several miniature microwave antenna designs are known. Conventional antenna designs are typically 1 to 2 mm in diameter and 5 to 7 mm in length and are operated at frequencies of from about 300 MHz up to about 2450 MHz.

Locally induced microwave hyperthermia for cancer therapy permits flexibility in treatment procedures for tumors of irregular volume and for tumors located deep within the body. Production of adequate thermal field distribution in superficial, accessible and deep-seated tumors is an important consideration. Limited depth of energy penetration has restricted the use of prior art antennas primarily to the heating of well localized tumors extending to depths of up to a few centimeters. Tumors in hollow viscera or cavities such as the oesophagus, cervix and prostate are amendable to treatment with intracavitary hyperthermia techniques. Interstitial hyperthermia techniques are employed for accessible tumors of large volume. A major limitation of prior art interstitial devices is maximization of thermal energy along the sides rather than at the tip of the applicator.

One prior art approach to enhancing the heating at the tip of the applicator is described in Lin, et al., Int. J. Hyperthermia, 3:37-47 (1987). The antenna described operates at 2450 MHz.

A 915 MHz applicator having a diameter in excess of 1 cm and hence too large for use in the treatment of nasopharyngeal cancer is described in Abstract Ce-9, p. 43, "Abstracts of Papers for the Thirty-Sixth Annual Meeting of the Radiation Research Society, Eighth Annual Meeting of the North American Hyperthermia Group", Philadelphia, Pa., Apr. 16-21, 1988, and was shown at that meeting.

SUMMARY OF THE INVENTION

It is an object of this invention to provide a hyperthermia applicator for treating cancers and other abnormal tissues, in which thermal energy is concentrated near the applicator tip.

It is also an object of the invention to provide a hyperthermia applicator of a size appropriate for the treatment of nasopharyngeal cancer which provides a high concentration of energy at the tip.

Another object of the invention is to provide an intracavitary hyperthermia applicator which has low power requirements and may be operated from portable machines.

A further object of the invention is to provide an intracavitary hyperthermia applicator which has an improved heating pattern as compared with prior art devices.

These objects are achieved by a microwave antenna, for example, a coaxial cable, having an inner conductor and an outer conductor, and in which the outer conductor is terminated in spaced relation to the end of the inner conductor and may be slotted at a location spaced from the end, defining a junction. A first sleeve of conductive material is shorted to the outer conductor at a predetermined spaced location rearwardly from the junction, and a second sleeve of conductive material is shorted to the outer conductor spaced rearwardly from the first sleeve. The sleeves extend forwardly in coaxial relationship with the cable end, but terminate at mutually spaced positions and all are spaced from the distal end of the inner conductor of the cable. A conductive body is affixed to the distal end of the inner conductor, and the entire active portion of the antenna is encapsulated in an insulating material such as epoxy. The dimensional relationships of the terminal ends of the sleeves and inner and outer conductors, their radial spacing from one another, the lengths of the sleeves, the location of the junction, and the geometry of the conductive body at the distal end of the inner conductor are all selected to achieve optimum results.

The outer diameter and the length of the applicators of the invention are selected to accommodate the bodily cavity in which a cancer may appear. Outer diameters may, for example, range from about 0.5 centimeters for nasopharyngeal cancer therapy to about 5 centimeters for cervical cancer treatment. Applicator lengths may correspondingly range from about 4.5 to about 10 centimeters.

For example, a first form of the invention is designed as a small applicator for use in nasopharyngeal cancer therapy. This applicator has an outer diameter of about 0.75 cm and a length of about 5.5 cm. The sleeves comprise copper foil or screen, and the conductive body comprises brass. The cable is preferably Micro coax, semi-rigid UT-250-A or RG-58A/U, and the sleeves are soldered to the outer conductor. When operated on a muscle phantom at 915 MHz, return losses of 10-15 DB are obtained, and maximum heatings of 1.3 and 0.85 degrees C/W-min. 1.15 cm apart are achieved at the tip and at the junction, respectively.

In a second form of the invention, the applicator is designed for the treatment of cervical cancer. This applicator comprises RG-9/U coaxial cable and has first and second coaxially arranged sleeves shorted at their rearward ends in spaced locations on the outer conductor of the cable, similarly to the nasopharyngeal form of the invention. However, the second or outer sleeve is spaced a greater distance radially from the first sleeve, and the conductive body at the distal tip of the inner conductor is a spiral. This applicator has an outer diameter of about 3 cm and an overall length of about 6.5 cm. Further, this applicator has distinct heating at the tip when operated at 915 MHz on a muscle phantom, with a maximum rate of heating of 0.25 degrees C/W-min.

Applicators of the invention described above can be effectively operated at 915 MHz with a 30 watt power generator, thus facilitating use with portable equipment at small rural hospitals or clinics. Deeper penetration is obtained at 915 MHz than at 2450 MHz, rendering the applicators more clinically useful than prior art designs.

BRIEF DESCRIPTION OF THE DRAWINGS

The foregoing and other objects and advantages of the invention will become apparent from the following detailed description and the accompanying drawings, in which like reference characters designate like parts throughout the several views, and wherein:

FIG. 1 is a longitudinal sectional view of a nasopharyngeal form of applicator according to the invention.

FIG. 2 is a view depicting the terminal exterior of the distal end cap of the applicator.

Computer generated FIGS. 3A, 3B, 3D and 3E show a thermographic temperature elevation of the applicator as shown in FIG. 1 operated at 915 MHz on a muscle phantom.

FIG. 3C illustrates the relationship of the applicator tip to the maximum heating peak shown in FIG. 3B.

Computer generated FIGS. 5A, 5B, 5C and 5D show a thermographic temperature elevation of the applicator shown in FIG. 4 operated at 915 MHz on a muscle phantom.

DETAILED DESCRIPTION OF THE PREFERRED EMBODIMENTS

Figure 4:
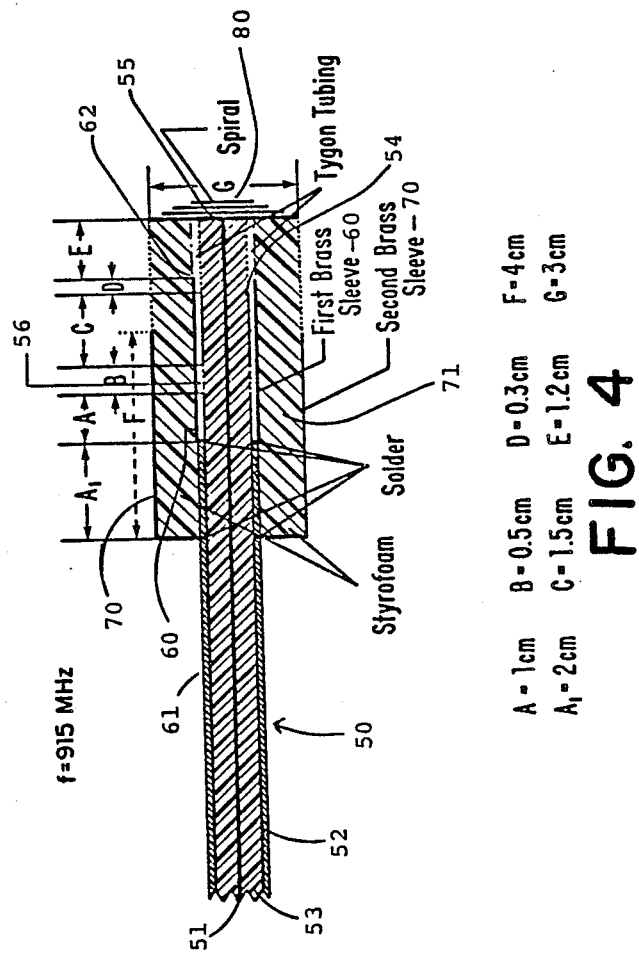
FIG. 4 is a longitudinal section of an intracavitary applicator for treatment of cervical cancer.

Referring more specifically to the drawings, a first form of intracavitary hyperthermia applicator in accordance with the invention is indicated generally at 10 in FIG. 1. This form of the invention is relatively small in size and is suitable for use in the treatment of nasopharyngeal cancer. The device is also useful in the treatment of other conditions, such as sinusitis, for example.

The applicator 10 comprises a length of Micro coax semi-rigid cable, UT-250-A or RG-58A/U, having an inner conductor 11 and a tubular outer conductor 12 spaced from the inner conductor by a layer of electrically non-conductive insulating material 13, such as, for example, polytetrafluoroethylene (Teflon, a trademark of DuPont). The inner and outer conductors have proximal and distal ends, and the distal end of the outer conductor is terminated short of the distal end 14 of the inner conductor. The outer conductor is also slotted at 15, spaced a distance "C" from its distal end 16. The slot has a longitudinal axial dimension "B".

A first sleeve 17 extends coaxially with the outer conductor and is maintained in radially outwardly spaced relationship thereto by a layer of non-conductive insulating material 18. The distal end 18 of the sleeve 17 extends beyond the end of the outer conductor by a distance "D", and is connected or shorted to the outer conductor at a location spaced a distance "A" rearwardly from the slot 15.

A second sleeve 19 extends coaxially with the first sleeve and is maintained in radially outwardly spaced relationship thereto by an insulating layer 21. The second sleeve is connected or shorted to the outer conductor 12 at a location spaced a distance "$A_1$" rearwardly of the point of connection of the first sleeve, and extends forwardly over the first sleeve a distance "F".

A cap 30 of conductive material, preferably brass, is affixed to the distal end 14 of the inner conductor 11 in transverse relationship to the axis of the applicator. The cap 30 has a diameter "G" approximately the same as the diameter of the second sleeve, and has a plurality of radial holes 31 extending from the center through the outer periphery at 90 degree intervals.

In a preferred construction, the dimensions of the various components of the applicator illustrated in FIGS. 1 and 2 are as follows: A=1 cm; $A_1$=1 cm; B=0.5 cm; C=1.5 cm; D=0.3 cm; E=1.2 cm; F=3.8 cm, and G=0.75 cm. The first and second sleeves are soldered to the outer conductor and comprise copper foil or screen. A layer 40 of epoxy is used to encapsulate the entire active section of the applicator. With the stated dimensions and when operated at 915 MHz and covered with a rubber finger cot or the like, this applicator produces a computer generated thermograph heating pattern as shown in FIGS. 3A, 3B, 3D and 3E. FIG. 3C shows the relationship of the applicator 10 to the tip of the maximum heating peak shown in FIG. 3D.

FIG. 3A depicts heating gradient lines. Maximum heating is shown at the point marked "+". In FIG. 3B, the peak, reflecting a maximum heating of about 1.3 degrees C. per minute watt (°C./W-min), corresponds to the point "+" in FIG. 3A. In FIG. 3D, the peak again shown at a maximum heating of 1.3 degrees C. per watt minute, corresponds to the "+" on FIG. 3A, as does the maximum peak in the three-dimensional FIG. 3E.

The second form of the invention is indicated generally at 50 in FIG. 4. This form of the invention comprises a length of RG=9/U coaxial cable having an inner conductor 51 and a tubular outer conductor 52 separated from the inner conductor by a layer of insulation 53. The outer or distal end 54 of the outer conductor is terminated short of the distal end 55 of the inner conductor by a distance "D" plus "E", and is slotted at 56 at a location spaced a distance "C" from its distal end. The slot has an axial dimension of "B".

A first sleeve 60 extends coaxially over the outer conductor and is maintained in radially outwardly spaced relationship thereto by a length of electrical insulating tubing 61, such as Tygon. The first sleeve extends at its distal end 62 a distance "D" beyond the distal end of the outer conductor, and is shorted or connected to the outer conductor at a location spaced a distance "A" rearwardly of the slot 56.

A second sleeve 70 is connected or shorted to the outer conductor at a location spaced a distance "$A_1$" rearwardly from the point of attachment of the first sleeve, and extends coaxially forwardly over the first sleeve a distance "F". The second sleeve is maintained in radially outwardly spaced relationship to the first sleeve by a layer of insulation 71, such as Styrofoam or the like, for example.

A body 80 of conductive material is secured to the forward or distal end of the inner conductor, and in the form of invention shown, comprises a spiral. The spiral has a diameter "G" approximately the same as the diameter of the second sleeve.

In a preferred construction of this form of the invention, the first and second sleeves are made of brass and the dimensional relationships are as follows: A=1 cm; $A_1$=2 cm; B=0.5 cm; C=1.5 cm; D=0.3 cm; E=1.2 cm; F=4 cm, and G=3 cm. When operated at a frequency at 915 MHz on a muscle phantom and with the stated dimensions as covered with a rubber finger cot or the like, this applicator produces a computer generated thermograph heating patterns and shown in FIGS. 5A, 5B, 5C and 5D.

FIGS. 5A, 5B, 5C and 5D are analogous to FIGS. 3A, 3B, 3D and 3E. The point of maximum heating appears at the place marked "+" in FIG. 5A. As appears from FIGS. 5B and 5C, a maximum heating of about 0.25 degrees C. per watt minute is obtained.

The first form of the invention described above is particularly suited to treatment of nasopharyngeal cancer, while the second form is best suited for treatment of cervical cancer. However, as noted, either form of the invention could be used in the treatment of other illnesses.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. An intracavitary hyperthermia applicator, comprising:
   outer and inner coaxial conductors having proximal ends and distal ends, respectively;
   insulating means between said conductors for electrically insulating them from one another;
   said outer conductor terminating in a distal end spaced proximally from the distal end of said inner conductor;
   said outer conductor having a slot formed therein spaced from the distal end thereof, defining a junction in the outer conductor;
   outer and inner tubular sleeves of conductive material disposed coaxially over a length of said outer conductor and each having a proximal end and a distal end;
   insulation means between said sleeves and between said inner sleeve and said outer conductor for electrically insulating them from one another;
   conductive attachment means securing the proximal ends of said sleeves to said outer conductor at points of attachment; and
   said outer sleeve terminating in a distal end spaced proximally from the distal end of said inner sleeve, said inner and outer sleeves both extending coaxially over the slot in the outer conductor.

2. An intracavitary hyperthermia applicator as defined by claim 1 in which said outer and inner coaxial conductors are a length of coaxial cable.

3. An intracavitary hyperthermia applicator as defined by claim 1 in which said outer coaxial conductor is circumferentially slotted.

4. An intracavitary hyperthermia applicator as claimed in claim 3, wherein:
   the distal end of the outer coaxial conductor terminates short of the distal end of the inner conductor,
   the distal end of the inner sleeve is spaced axially between the distal ends of the inner and outer conductors, and the distal end of the outer sleeve terminates short of the distal ends of both the first sleeve and the outer conductor.

5. An intracavitary hyperthermia applicator as claimed in claim 4, wherein:
   the length of the slot in the outer conductor is equal to substantially one-half the spacing between the points of attachment of the inner and outer sleeves to the outer conductor.

6. An intracavitary hyperthermia applicator as claimed in claim 5, wherein:
   the spacing between the points of attachment of the inner and outer sleeves to the outer conductor is substantially equal to the spacing between the slot in the outer conductor and the point of attachment of the inner sleeve to the outer conductor.

7. An intracavitary applicator as defined by claim 1 having a maximum outer diameter of from about 0.5 to about 5.0 centimeters and a length of from about 4.5 to about 10 centimeters.

8. An intracavitary applicator as defined by claim 1, in which:
   the applicator has a length of about 5.5 cm and a diameter of about 0.75 cm; the points of attachment of the inner and outer sleeves to the outer conductor are spaced apart about 1 cm; the distal end of the inner sleeve is spaced distally relative to the distal end of the outer conductor a distance of about 0.3 cm; the distal end of the inner sleeve is spaced proximally relative to the distal end of the inner conductor a distance of about 1.2 cm; and the outer conductor is slotted at a location spaced approximately 1.5 cm proximally from the distal end of the outer conductor.

9. An intracavitary hyperthermia applicator as claimed in claim 8, wherein:
   the inner and outer sleeves are copper foil; and
   the inner and outer coaxial conductors are part of a length of semi-rigid RG=58A/U coaxial cable.

10. An intracavitary applicator as defined by claim 1, in which:
    the applicator has a length of about 6.5 cm and a diameter of about 3 cm; the points of attachment of the inner and outer sleeves to the outer conductor are spaced apart about 1 cm; the distal end of the inner sleeve is spaced distally relative to the distal end of the outer conductor a distance of about 0.3 cm; the distal end of the inner sleeve is spaced proximally relative to the distal end of the inner conductor a distance of about 1.2 cm; and the outer conductor is slotted at a location spaced approximately 1.5 cm proximally from the distal end of the outer conductor.

11. An intracavitary hyperthermia applicator as claimed in claim 10, wherein:
    the inner and outer sleeves are brass; and
    the inner and outer coaxial conductors are part of a length of semi-rigid RG=9/U coaxial cable.

* * * * *